(12) United States Patent
Sugimoto et al.

(10) Patent No.: US 8,337,399 B2
(45) Date of Patent: Dec. 25, 2012

(54) ENDOSCOPE APPARATUS AND SCANNING ENDOSCOPE PROCESSOR

(75) Inventors: Hideo Sugimoto, Tokyo (JP); Kohei Iketani, Saitama (JP)

(73) Assignee: Hoya Corporation, Tokyo (JP)

( * ) Notice: Subject to any disclaimer, the term of this patent is extended or adjusted under 35 U.S.C. 154(b) by 546 days.

(21) Appl. No.: 12/614,595

(22) Filed: Nov. 9, 2009

(65) Prior Publication Data

US 2010/0121143 A1  May 13, 2010

(30) Foreign Application Priority Data

Nov. 10, 2008 (JP) ................................. 2008-288190

(51) Int. Cl.
*A61B 1/06* (2006.01)
(52) U.S. Cl. ........................................ 600/173; 600/168
(58) Field of Classification Search ................. 600/109, 600/168, 173
See application file for complete search history.

(56) References Cited

U.S. PATENT DOCUMENTS

| 6,147,822 | A | 11/2000 | Yamada et al. |
| 6,294,775 | B1 | 9/2001 | Seibel et al. |
| 2005/0288553 | A1 | 12/2005 | Sugimoto |
| 2006/0167344 | A1 | 7/2006 | Mizumo |
| 2007/0035797 | A1 | 2/2007 | Kanai |
| 2008/0161648 | A1 | 7/2008 | Karasawa |
| 2008/0231692 | A1 | 9/2008 | Higuchi et al. |
| 2009/0028407 | A1 | 1/2009 | Seibel et al. |
| 2009/0137893 | A1* | 5/2009 | Seibel et al. .................. 600/407 |

FOREIGN PATENT DOCUMENTS

| JP | 2003-46716 | 2/2003 |
| JP | 2003-121755 | 4/2003 |
| JP | 3943927 | 4/2007 |

\* cited by examiner

*Primary Examiner* — Clayton E Laballe
*Assistant Examiner* — Noam Reisner
(74) *Attorney, Agent, or Firm* — Greenblum & Bernstein, P.L.C.

(57) ABSTRACT

An endoscope apparatus, comprising an imaging controller, a receiver, and an image generator, is provided. The imaging controller makes an optical image to be captured so that the amount of optical information to be captured per a certain area size for an enlarged observation area is greater than that for a normal observation area. The receiver receives the optical information as a pixel signal. The image generator generates a normal image signal corresponding to a normal image on the basis of the pixel signals captured within the normal observation area and a part of the pixel signals captured within the enlarged observation area. The image generator generates an enlarged image signal corresponding to an enlarged image on the basis of the pixel signals captured within the enlarged observation area.

6 Claims, 12 Drawing Sheets

ENDOSCOPE APPARATUS AND SCANNING ENDOSCOPE PROCESSOR

BACKGROUND OF THE INVENTION

1. Field of the Invention

The present invention relates to an endoscope apparatus that enables minute images with different enlargement magnifications to be simultaneously displayed.

2. Description of the Related Art

An endoscope is used for identifying an internal lesion in a body. Especially for identifying a lesion such as a malignant tumor, it is required to use enlargement to observe the form of blood vessels near the surface of an organ. For such a requirement, an endoscope for magnifying an observation and an endoscope that can operate in either normal observation mode or magnified observation mode are proposed.

Using the endoscope for magnified observation prohibits an entire observation area from being observed because an enlarged image is constantly displayed. Accordingly, it is difficult to determine which section of an area is displayed with the enlargement of an entire area that is desired for observation.

In addition, even when using an endoscope that can be changed to either normal observation mode or magnified observation mode, when the distal end of an insertion tube shifts during observation with enlargement; it is difficult to determine which particular area is displayed with enlargement of the entire area.

Japanese Patent No. 3943927 discloses the single fiber endoscope that can provide an image with enlargement. However, as described above, it is difficult to determine which particular area is displayed with enlargement of the entire area.

SUMMARY OF THE INVENTION

Therefore, an object of the present invention is to provide an endoscope apparatus that enables an observer to easily determine which enlarged area is displayed.

According to the present invention, an endoscope apparatus, comprising an imaging controller, a receiver, and an image generator, is provided. The imaging controller makes an optical image to be captured so that the amount of optical information to be captured per a certain area size for an enlarged observation area is greater than that for a normal observation area. The enlarged observation area is a part of an area defined in an observation area of which an optical image should be generated. The normal observation area is the observation area excluding the enlarged observation area. The receiver receives the optical information as a pixel signal. The pixel signal is an electric signal. The image generator generates a normal image signal corresponding to a normal image on the basis of the pixel signals captured within the normal observation area and a part of the pixel signals captured within the enlarged observation area. The image generator generates an enlarged image signal corresponding to an enlarged image on the basis of the pixel signals captured within the enlarged observation area. The normal image and the enlarged image are images of the normal and enlarged observation areas, respectively.

According to the present invention, a scanning endoscope processor, comprising a first controller, a photoelectric converter, a second controller, and an image generator, is provided. The scanning endoscope processor has first second channels and an actuator. The first controller controls the actuator to move the first channel along a predetermined course. The first channel transmits illumination light and makes the illumination light incident on an observation area of which an optical image is generated. The actuator moves the first channel so that the observation area is scanned with the illumination light incident from the first channel. The photoelectric converter captures optical information transmitted by the second channel and generates a pixel signal according to the amount of light corresponding to the optical information. The second channel transmits the optical information at locations illuminated by the illumination light incident from the first channel. The second controller adjusts a first velocity and/or a first cycle so that the number of pixel signals generated per a certain area size for an enlarged observation area is greater than that for a normal observation area. The first channel is moved at the first velocity. The photoelectric converter generates the pixel signals in the first cycle. The enlarged observation area is a part of an area defined in an entire observation area of which an optical image is generated. The normal observation area is the observation area excluding the enlarged observation area. The image generator generates a normal image signal corresponding to a normal image on the basis of the pixel signals captured within the normal observation area and a part of the pixel signals captured within the enlarged observation area. The image generator generates an enlarged image signal corresponding to an enlarged image on the basis of the pixel signals captured within the enlarged observation area. The normal image and the enlarged image are images of the normal and enlarged observation areas, respectively.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

The present invention is described below with reference to the embodiment shown in the drawings.

Figure 1:
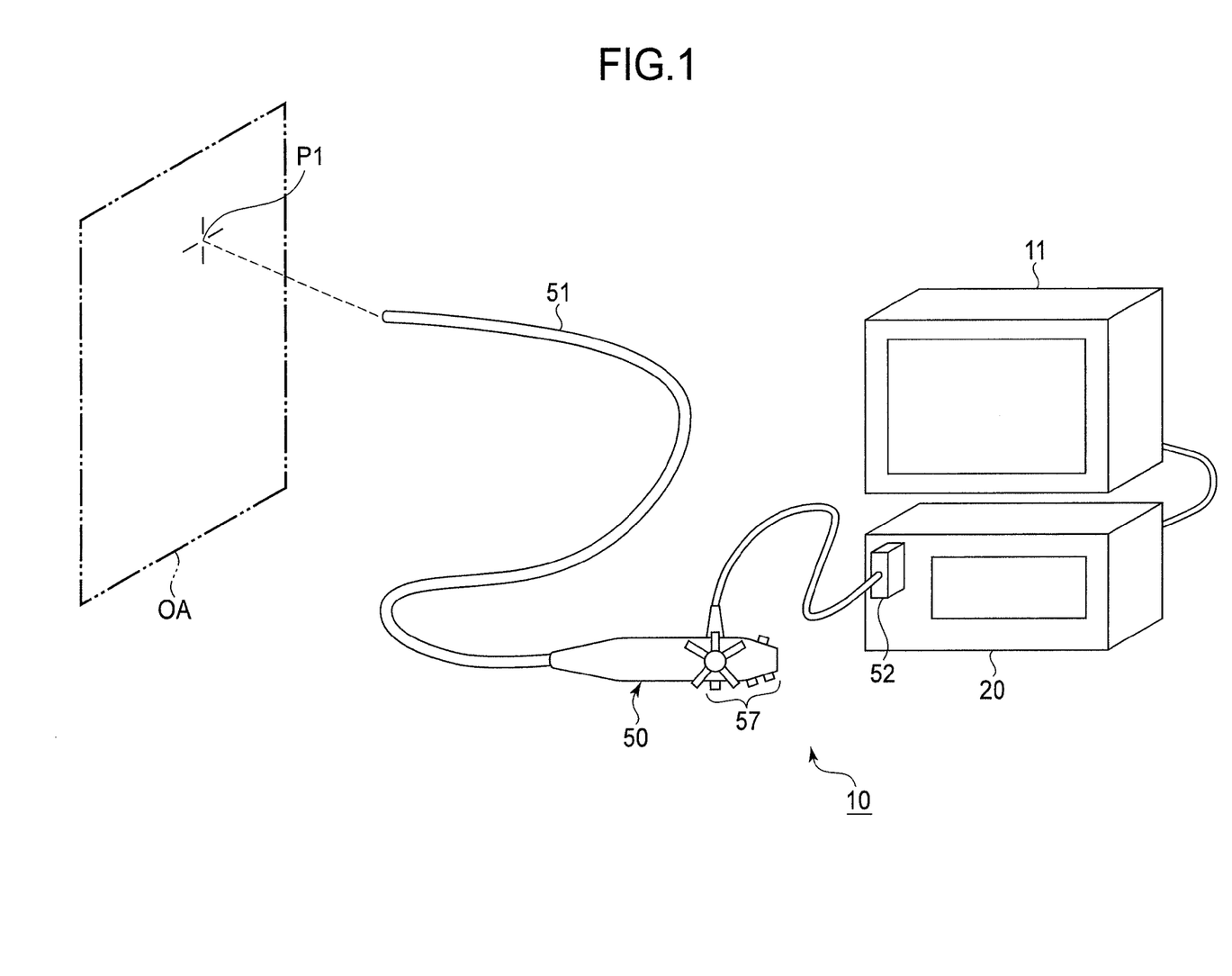
FIG. 1 illustrates the schematic appearance of an endoscope apparatus of the embodiments of the present invention.

In FIG. 1, the endoscope apparatus 10 comprises a scanning endoscope processor 20, a scanning endoscope 50, and a monitor 11. The scanning endoscope processor 20 is connected to the scanning endoscope 50 and the monitor 11. Hereinafter, the head ends of an illumination fiber (not depicted in FIG. 1) and image fibers (not depicted in FIG. 1) are the ends mounted in the distal end of the insertion tube 51 of the scanning endoscope 50. In addition, the base ends of the illumination fiber and the image fibers are the ends mounted in the connector 52 that connects to the scanning endoscope processor 20.

The scanning endoscope processor 20 provides light that is shined on an observation area (see "OA" in FIG. 1). The light emitted from the scanning endoscope processor 20 is transmitted to the distal end of the insertion tube 51 through the illumination fiber (first channel), and is directed towards one point (see "P1" in FIG. 1) in the observation area. Light reflected from the illuminated point is transmitted from the distal end of the insertion tube 51 to the scanning endoscope processor 20.

The direction of the head end of the illumination fiber is changed by a fiber actuator (not depicted in FIG. 1). By changing the direction, the observation area is scanned with the light emitted from the illumination fiber. The fiber actuator is controlled by the scanning endoscope processor 20.

The scanning endoscope processor 20 receives reflected light that is scattered at the illuminated point, and generates a pixel signal according to the amount of received light. One frame of an image signal is generated by generating pixel signals corresponding to the illuminated points dispersed throughout the observation area. The generated image signal is transmitted to the monitor 11, where an image corresponding to the received image signal is displayed.

Figure 2:
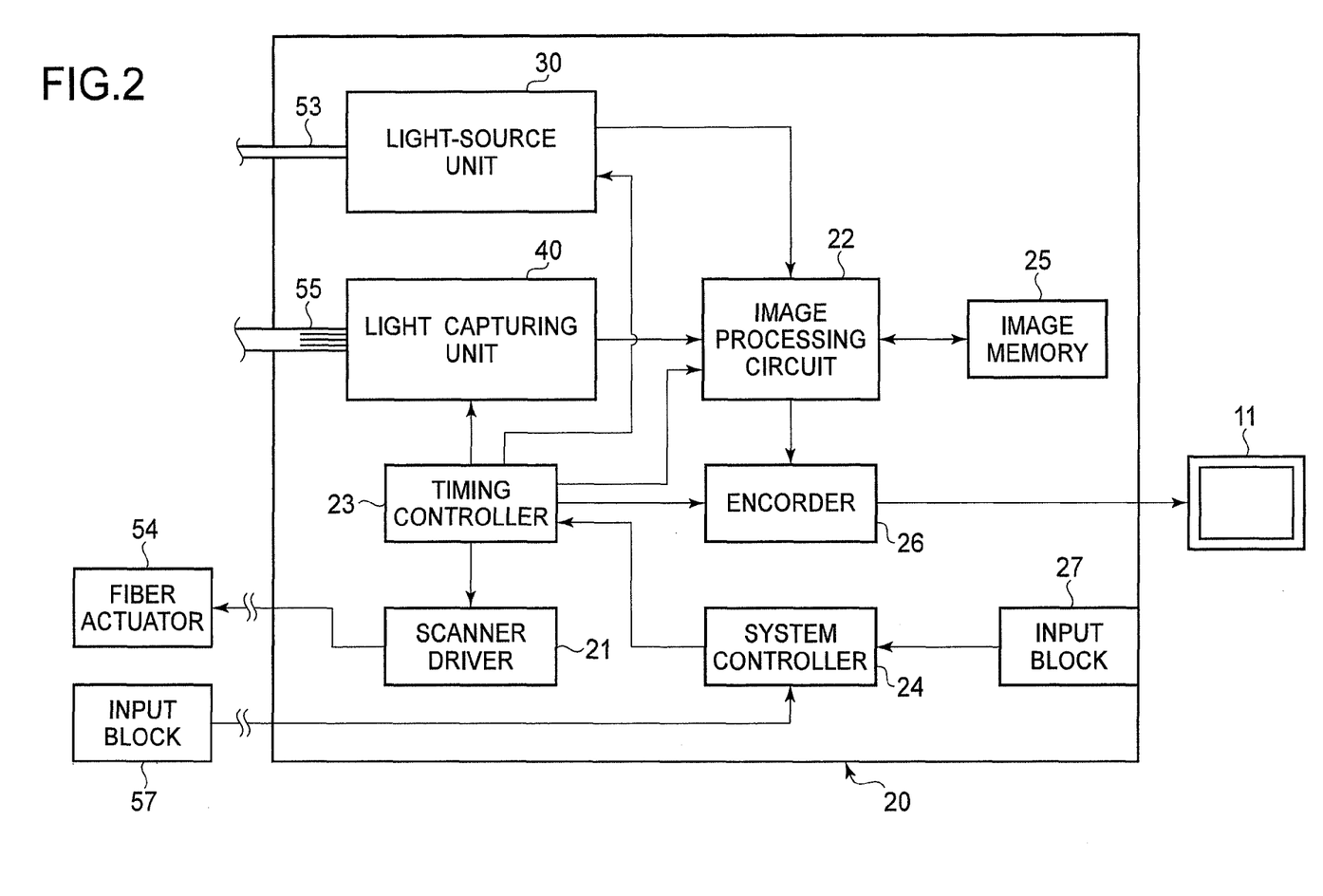
FIG. 2 is a block diagram schematically showing the internal structure of the scanning endoscope processor for the scanning endoscope.

As shown in FIG. 2, the scanning endoscope processor 20 comprises a light-source unit 30, a light capturing unit 40, a scanner driver 21, an image processing circuit 22, a timing controller 23, a system controller 24, and other components.

As described later, the light-source unit 30 provides the illumination fiber 53 with the light to illuminate an observation area. The scanning driver 21 controls the fiber actuator 54 to move the head end of the illumination fiber 53. The reflected light at the illuminated point is transmitted to the scanning endoscope processor 20 by the scanning endoscope 50. The transmitted light is made incident on the light capturing unit 40.

The light capturing unit 40 generates a pixel signal according to the amount of the reflected light. The pixel signal is transmitted to the image processing circuit 22, which stores the received pixel signal in the image memory 25. Once pixel signals corresponding to the illuminated points dispersed throughout the observation area have been stored, the image processing circuit 22 carries out predetermined image processing on the pixel signals, and then one frame of the image signal is transmitted to the monitor 11 via the encoder 26.

By connecting the scanning endoscope 50 to the scanning endoscope processor 20, optical connections are made between the light-source unit 30 and the illumination fiber 53 mounted in the scanning endoscope 50, and between the light capturing unit 40 and the image fibers 55. In addition, by connecting the scanning endoscope 50 to the scanning endoscope processor 20, the fiber actuator 54 mounted in the scanning endoscope 50 is electrically connected to the scanning driver 21.

The timing for carrying out the operations of the light-source unit 30, the light capturing unit 40, the image processing circuit 22, the scanning driver 21, and the encoder 26 is controlled by the timing controller 23. In addition, the timing controller 23 and other components of the endoscope apparatus 10 are controlled by the system controller 24.

A user can input certain commands to the input block 27, which comprises a front panel (not depicted) and other mechanisms. In addition, the scanning endoscope 50 comprises an input block 57 (see FIGS. 1 and 2). A user can input certain commands to the input block 57 of the scanning endoscope 50. It is more convenient for a user to input commands to the input block 57 of the scanning endoscope 50.

Figure 3:
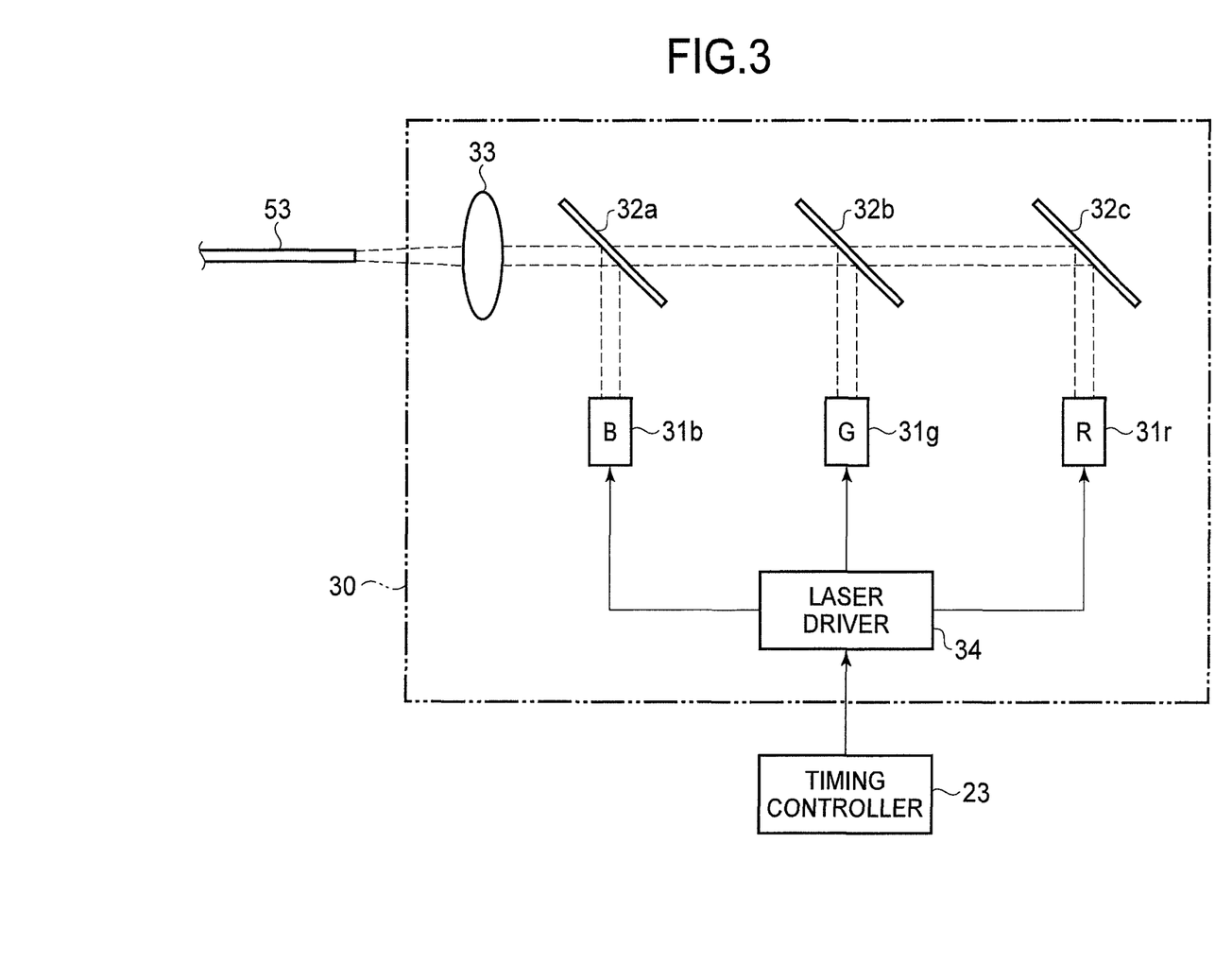
FIG. 3 is a block diagram schematically showing the internal structure of the light-source unit.

As shown in FIG. 3, the light-source unit 30 comprises a red laser 31r, a green laser 31g, a blue laser 31b, first to third filters 32a, 32b, and 32c, a condenser lens 33, a laser driver 34, and other components.

The red, green, and blue lasers 31r, 31g, and 31b emit red, green, and blue laser beams, respectively.

The first filter 32a reflects the band of blue light that the blue laser 31b emits, and transmits the other bands. The second filter 32b reflects the band of green light that the green laser 31g emits, and transmits the other bands. The third filter 32c reflects the band of red light that the red laser 31r emits, and transmits the other bands.

The condenser lens 33, the first filter 32a, the second filter 32b, the third filter 32c are arranged in the incident direction of the base end of the illumination fiber 53, which is connected to the light-source unit 30.

The first to third filters 32a, 32b and 32c are fixed so that the surfaces of the filters are inclined by 45 degree against the axis direction of the illumination fiber 53. The blue laser beam emitted by the blue laser 31b is reflected toward the base end of the illumination fiber 53 by the first filter 32a. The green laser beam emitted by the green laser 31g is reflected toward the base end of the illumination fiber 53 by the second filter 32b. The red laser beam emitted by the red laser 31r is reflected toward the base end of the illumination fiber 53 by the third filter 32c.

The blue laser beam reflected by the first filter 32a is condensed by the condenser lens 33, and made incident on the base end of the illumination fiber 53. The green laser beam reflected by the second filter 32b and transmitted by the first filter 32a is condensed by the condenser lens 33, and made incident on the base end of the illumination fiber 53. The red laser beam reflected by the third filter 32c and transmitted by the first and second filters 32a and 32b is condensed by the condenser lens 33, and made incident on the base end of the illumination fiber 53.

Upon observing a real-time image in the peripheral area of the insertion tube 51, the red, green, and blue laser beams are mixed into a white laser beam, which is supplied to the illumination fiber 53.

The laser driver 34 drives the red, green, and blue lasers 31r, 31g, and 31b. In addition, on the basis of the control of the timing controller 23, the laser driver 34 controls the light-on and -off timing for the lasers 31r, 31g, and 31b.

Figure 4:
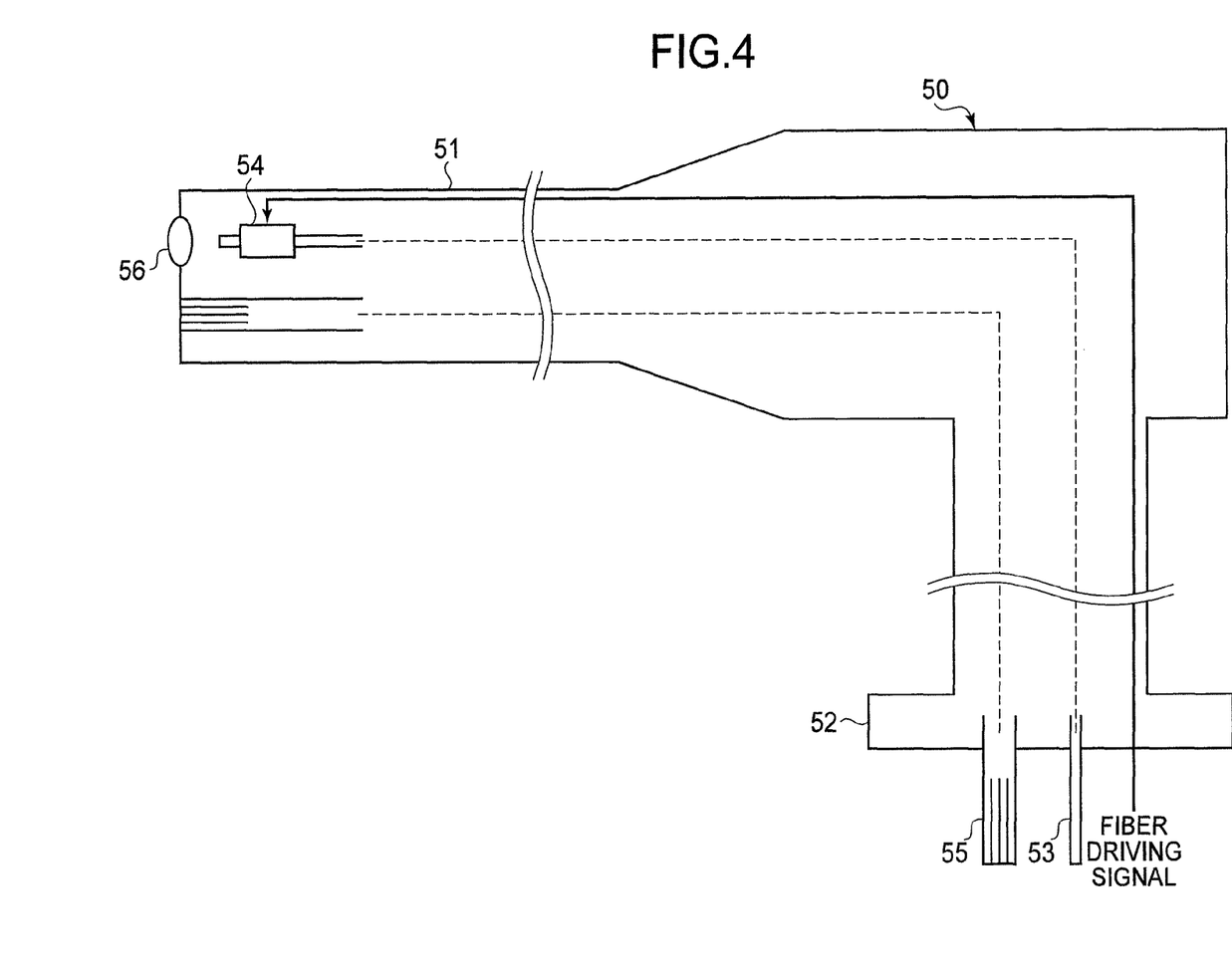
FIG. 4 is a block diagram schematically showing the internal structure of the scanning endoscope.

Next, the structure of the scanning endoscope 50 is explained. As shown in FIG. 4, the scanning endoscope 50 comprises the illumination fiber 53, the image fibers 55, a condenser lens 56, the fiber actuator 54, and other components. It should be noted that the arrangement of each component is conceptual, and the practical arrangements are not limited in the figure.

The illumination fiber 53 and the image fibers 55 are mounted from the connector 52 to the distal end of the insertion tube 51 inside of the scanning endoscope 50. As described above, the white laser beam emitted by the light-source unit 30 is incident on the base end of the illumination fiber 53. The incident white laser beam is transmitted to the head end of the illumination fiber 53.

The fiber actuator 54 is mounted near the head end of illumination fiber 53. The fiber actuator 54 comprises piezoelectric elements (not depicted). The piezoelectric elements incline the illumination fiber 53 in the first and second diameter directions of the illumination fiber 53. The first and second diameter directions are perpendicular to the axis directions of the head end of the illumination fiber 53.

The angle of inclination of the illumination fiber is adjusted on the basis of a fiber driving signal transmitted from the scanning driver 21. The observation area is scanned with the light by vibrating the head end of the illumination fiber 53 so as to vary the angle of inclination.

The light is emitted from the illumination fiber 53 toward one point (see "P2" in FIG. 5) within the observation area. The reflected light is scattered at the point illuminated by the light. The scattered, reflected light is incident on the head end of the image fibers 55.

A plurality of the image fibers 55 are mounted in the scanning endoscope 50. The head ends of the image fibers 55 are arranged around the condenser lens 56 (see FIG. 5). The light that is scattered and reflected from the point in the observation area is incident on all the image fibers 55.

Figure 5:
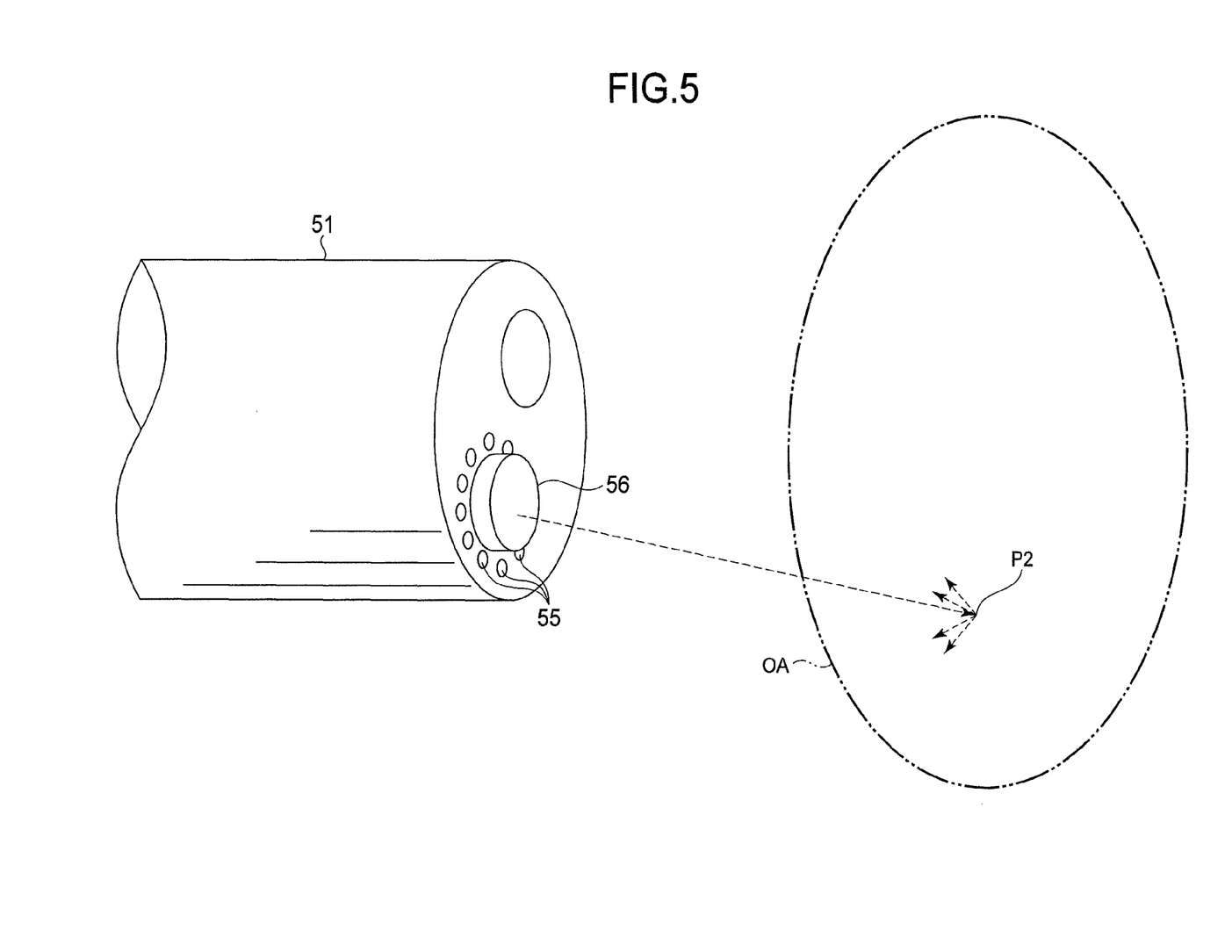
FIG. 5 illustrates the condition when light is incident from the condenser lens.

The reflected light incident on the head end of the image fibers 55 is transmitted to the base end. As described above, the base end of the image fibers 55 are optically connected to the light capturing unit 40. The reflected light transmitted to the base end is incident on the light capturing unit 40.

Figure 6:
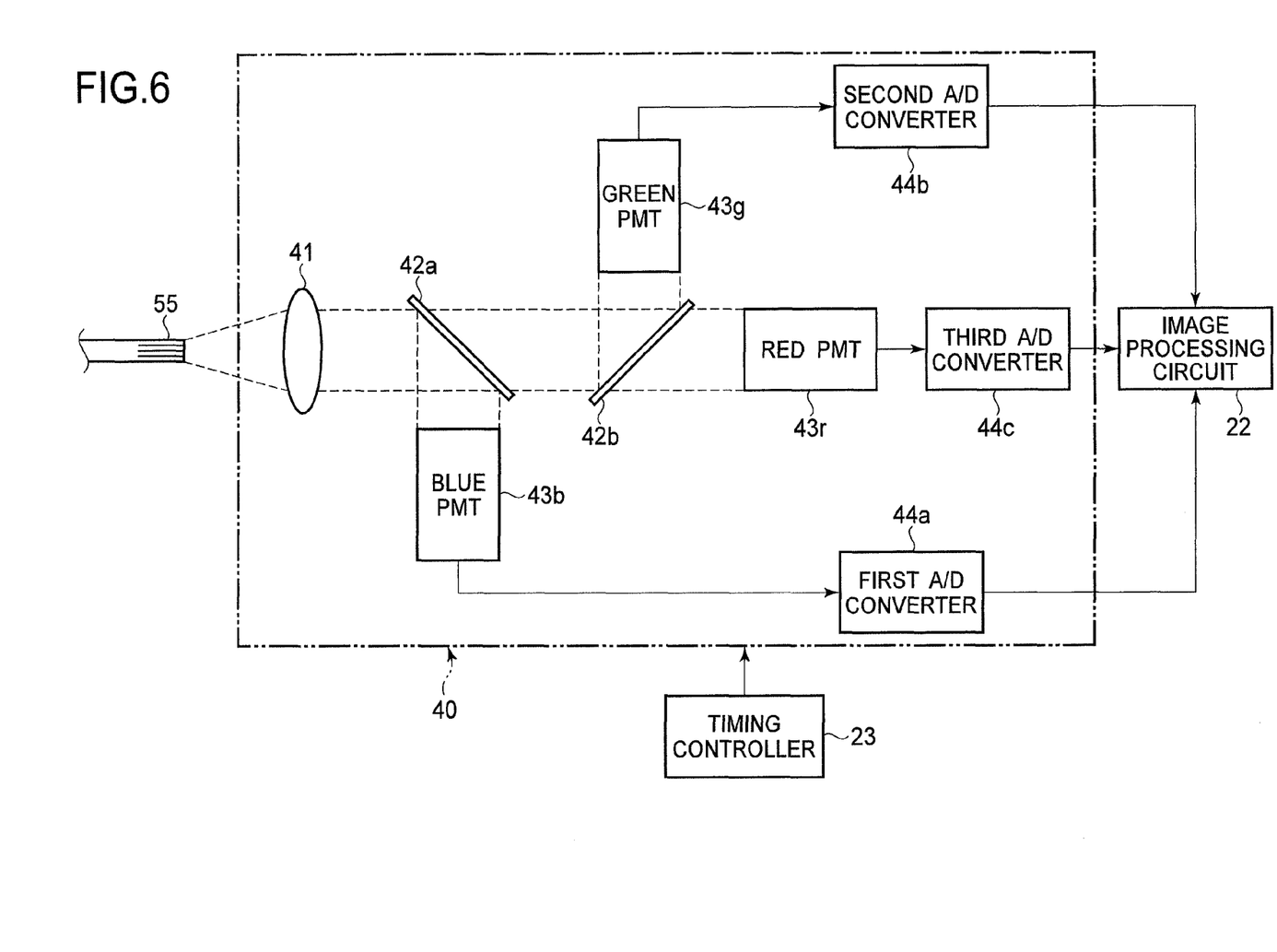
FIG. 6 is a block diagram schematically showing the internal structure of the light capturing unit.

As shown in FIG. 6, the light capturing unit 40 comprises a collimating lens 41, first and second beam splitters 42a and 42b, red, green, and blue photomultiplier tubes (PMTs) 43r, 43g, and 43b, and first to third A/D converters 44a to 44c.

The collimating lens 41 and the first and second beam splitters 42a and 42b are arranged in the direction of emission away from the base end of the image fibers 55. The light incident from the bundle of a plurality of image fibers 55 passes through the collimating lens 41 before arriving at the first beam splitter 42a.

The first beam splitter 42a is inclined against the light incident from the collimating lens 41, and reflects a blue light component so that the reflected blue light component is made incident on the blue PMT 43b. In addition, the first beam splitter 42a transmits the bands of light excluding the band of the blue light, and lets the transmitted light reach the second beam splitter 42b.

The second beam splitter 42b is inclined against the light passing through the first beam splitter 42a, and reflects a green light component so that the reflected green light component is made incident on the green PMT 43g. In addition, the second beam splitter 42b transmits the bands of light excluding the band of the green light, so that the transmitted light is incident on the red PMT 43r.

The red, green, and blue PMTs 43r, 43g, and 43b generate pixel signals according to the amounts of the red, green, and blue light components of the reflected light that are scattered at the point of illumination and transmitted by the image fibers 55.

A red band filter that transmits only the same band of light as the red laser beam emitted by the red laser 31r can be mounted on the light-receiving surface of the red PMT 43r. A green band filter that transmits only the same band of light as the green laser beam emitted by the green laser 31g can be mounted on the light-receiving surface of the green PMT 43g. A blue band filter that transmits only the same band of light as the blue laser beam emitted by the blue laser 31b can be mounted on the light-receiving surface of the blue PMT 43b.

The pixel signals generated by the blue, green, and red PMTs 43b, 43g, and 43r are digitized by the first, second, and third A/D converters 44a, 44b, and 44c, respectively. The digitized pixel signals are transmitted to the image processing circuit 22.

The first to third A/D converters 44a to 44c are controlled by the timing controller 23. On the basis of the control of the timing controller 23, the cycle of the analog-to-digital (A/D) conversion processing is adjusted. By adjusting the cycle of the A/D conversion processing, the cycle to generate the digitized pixel signals is adjusted.

The image processing circuit 22 receives a timing signal necessary for control of the scanning driver 21 that is also transmitted from the timing controller 23. The image processing circuit 22 estimates the point where the white laser beam is shone on the basis of the timing signal, and stores the pixel signals at the address of the image memory 25 corresponding to the estimated point.

The image memory 25 comprises a normal image storage area and an enlarged image storage area. When a normal image should be produced, pixel signals are stored at the address in the normal image storage area. On the other hand, when an enlarged image should be produced, pixel signals are stored at the address in the enlarged image storage area.

As described above, the observation area is scanned with the white laser beam, pixel signals are generated on the basis of the reflected light at the respective points illuminated by the white light beam, and the generated pixel signals are stored at the addresses corresponding to the points. The image signal corresponding to the observation area comprises the pixel signals corresponding to the points from the scan-start point to the scan-end point.

The endoscope apparatus 10 has a normal image observation function and an enlarged image observation function. The operations of the components of the endoscope apparatus 10 upon carrying out the normal and enlarged image observation functions are explained below.

Figure 7:
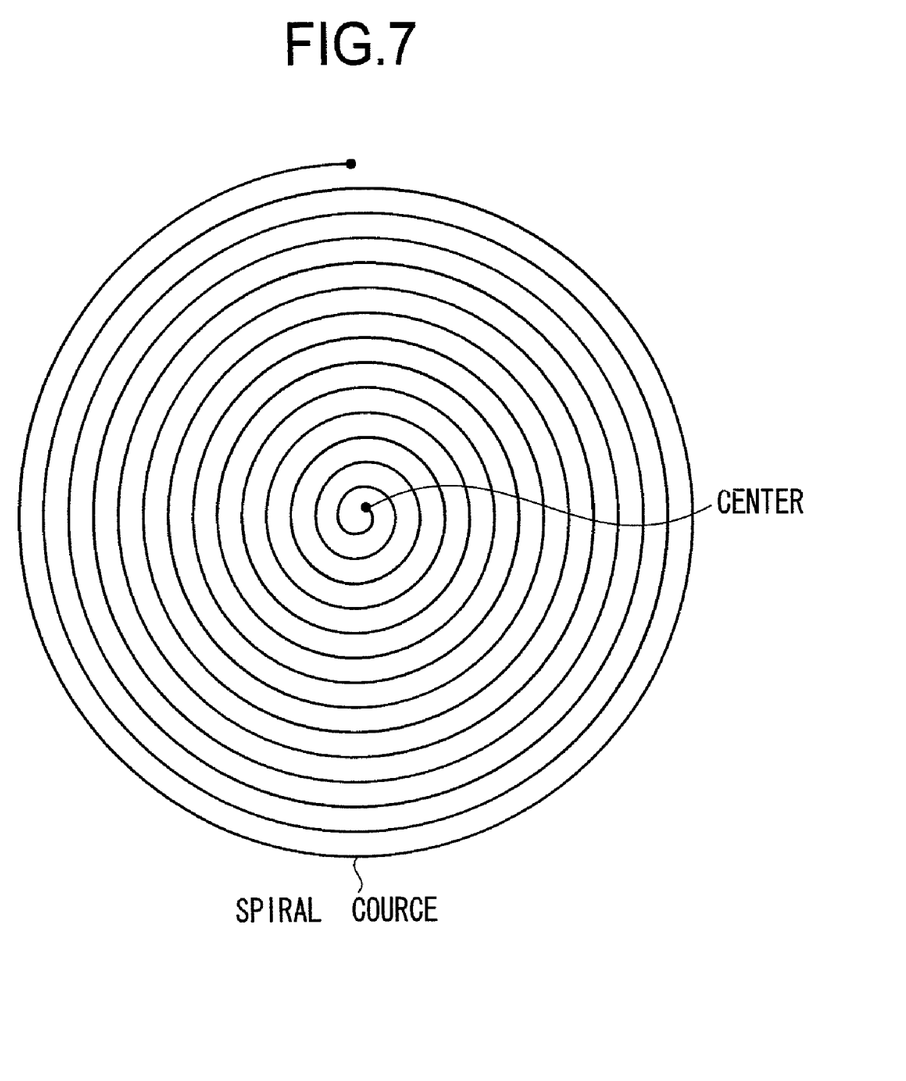
FIG. 7 illustrates a spiral course along which the head end of the illumination fiber is moved.

Upon carrying out the normal image observation function, the fiber actuator 54 drives the illumination fiber 53 so that the head end of the illumination fiber 53 is moved along the spiral course shown in FIG. 7. In addition, the illumination fiber 53 is driven so that the head end rotates at the constant angular velocity of "ω". Because the head end rotates at the constant angular velocity, the farther the head end is from the center of the spiral course, the faster the head end of the illumination fiber 53 moves along the spiral course.

Upon carrying out the normal image observation function, the cycle of the A/D conversion processing by the first to third A/D converters 44a to 44c are adjusted by the timing controller 23 so that the cycle of "t" is inversely proportional to the distance of "r" between the head end and the center (i.e., r×t=constant).

Figure 8:
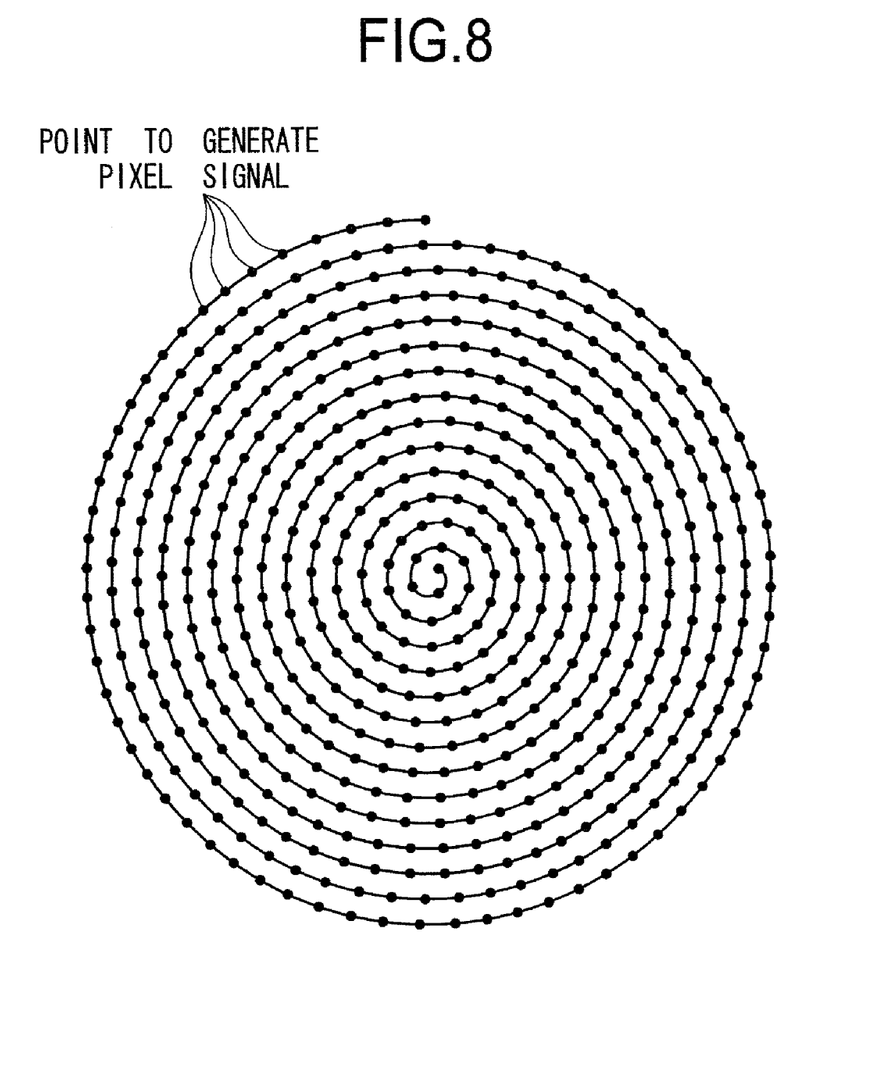
FIG. 8 illustrates the points that generate the pixel signals to explain the number of the pixel signals generated along the spiral course per a certain area size.

By adjusting the cycle of the A/D conversion described above, a space between the points where the neighboring pixel signals are generated can be constant as defined by r×ω×t. Accordingly, as shown in FIG. 8, the number of generated pixel signals per a certain area size is constant in spite of the velocity of the moving head end of the illumination fiber 53. In other words, the number of pixel signals to capture light per a certain area size is constant (see the black points in FIG. 8).

Figure 9:
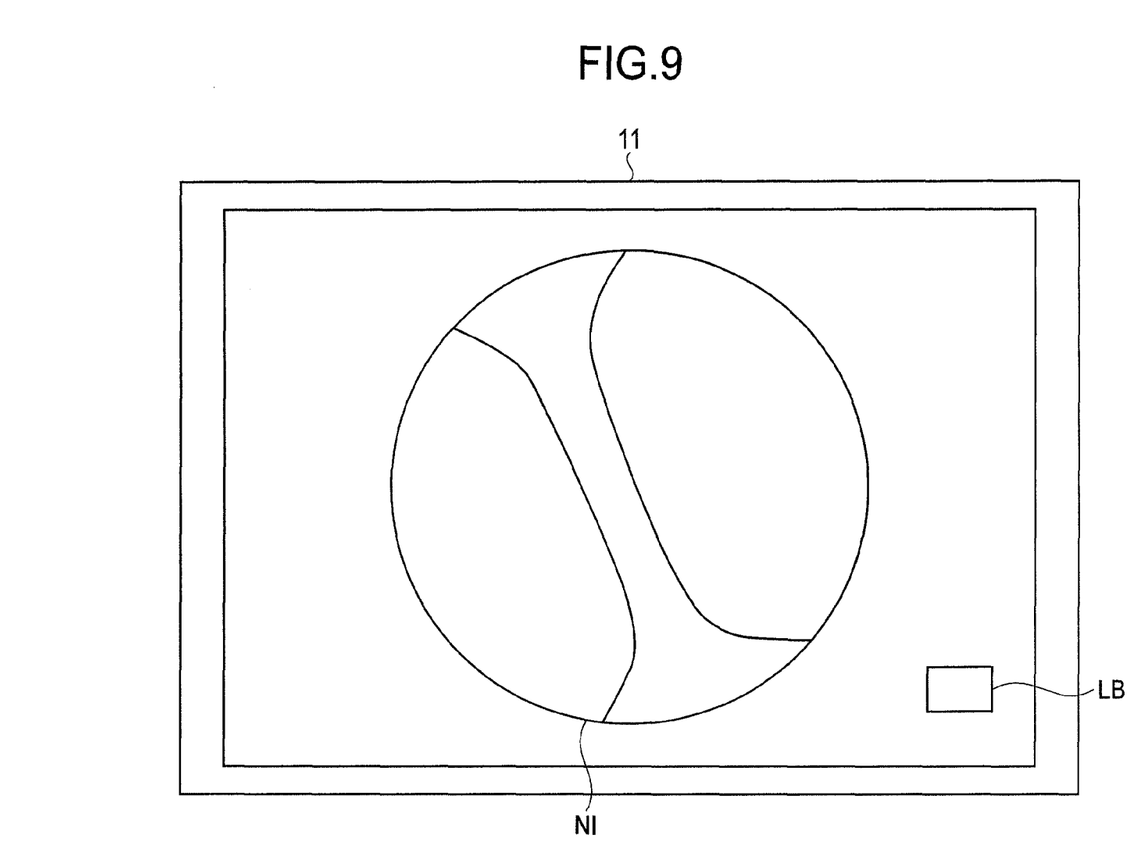
FIG. 9 illustrates the normal image displayed on the monitor while carrying out the normal image observation function.

The image processing circuit 22 stores all the received pixel signals at their corresponding addresses in the normal image storage area. As described above, the generated image signal is transmitted to the monitor 11. And then, a normal image (see "NI" in FIG. 9) is displayed that includes a field of vision large enough for an observer to look for a lesion.

When a user either inputs a command to carry out an enlarged image observation function or depresses a button (see "LB" in FIG. 9) displayed with the normal image using a pointing device (not depicted), such as a mouse, the enlarged image observation function is carried out.

Figure 10:
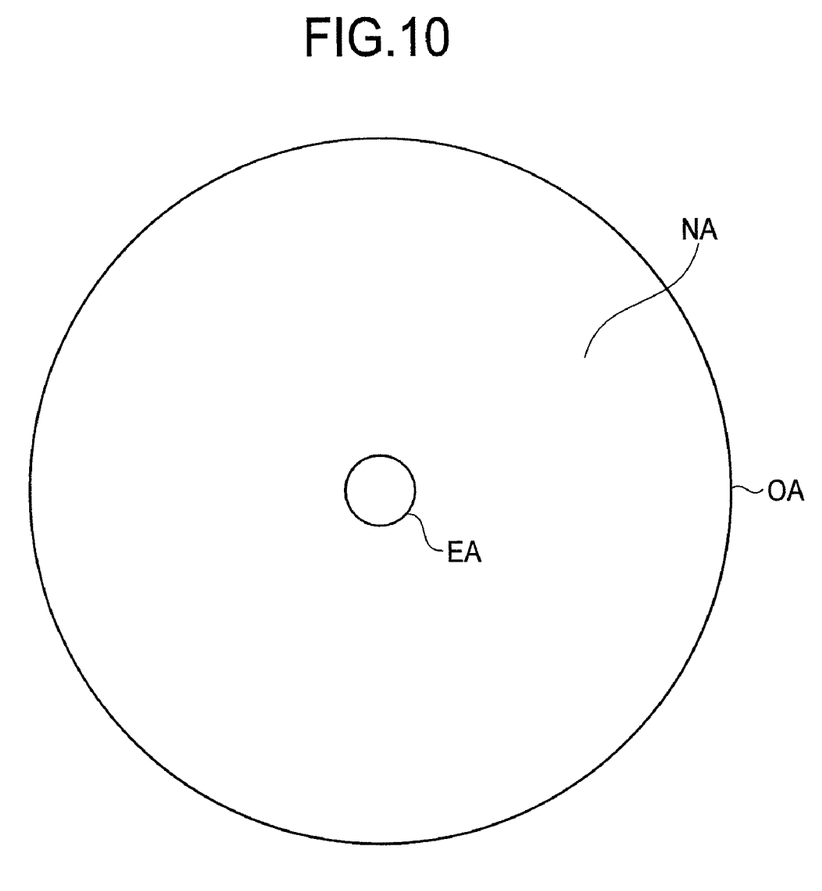
FIG. 10 shows the location and the size of the enlarged area of observation in the entire observation area.

The area that includes the center of the observation area (see "OA" in FIG. 10), which is 1/10 as large as the size of the observation area, is defined as an enlarged observation area (see "EA" in FIG. 10). In addition, the area in the observation area excluding the enlarged observation area is defined as a normal observation area (see "NA").

Also upon carrying out the enlarged image observation function, the fiber actuator 54 drives the illumination fiber 53 so that the head end of the illumination fiber 53 is moved along the same spiral course as that in the normal image observation function. In addition, the illumination fiber 53 is driven so that the head end rotates at the same angular velocity of "ω" as that in the normal image observation function.

When the head end of the illumination fiber 53 faces toward the points in the normal observation area during the enlarged image observation function, the timing controller 23 adjusts the cycle of the A/D conversion processing so that the product of the cycle "t" and the distance "r" is a constant value "k".

In addition, when the head end of the illumination fiber 53 faces toward the points in the enlarged observation area during the enlarged image observation function, the timing controller 23 adjusts the cycle of the A/D conversion processing so that the product of the cycle "t" and the distance "r" is a constant value of "k/10".

By adjusting the cycle of the A/D conversion described above, a space between the points where the neighboring pixel signals are generated can be held constant at k×ω and (k×ω)/10 while the head end of the illumination fiber 53 faces toward the point in the normal observation area and the enlarged observation area, respectively. In addition, a space between the points where the neighboring pixel signals are generated for the enlarged observation area is 1/10 as long as that for the normal observation area.

Figure 11:
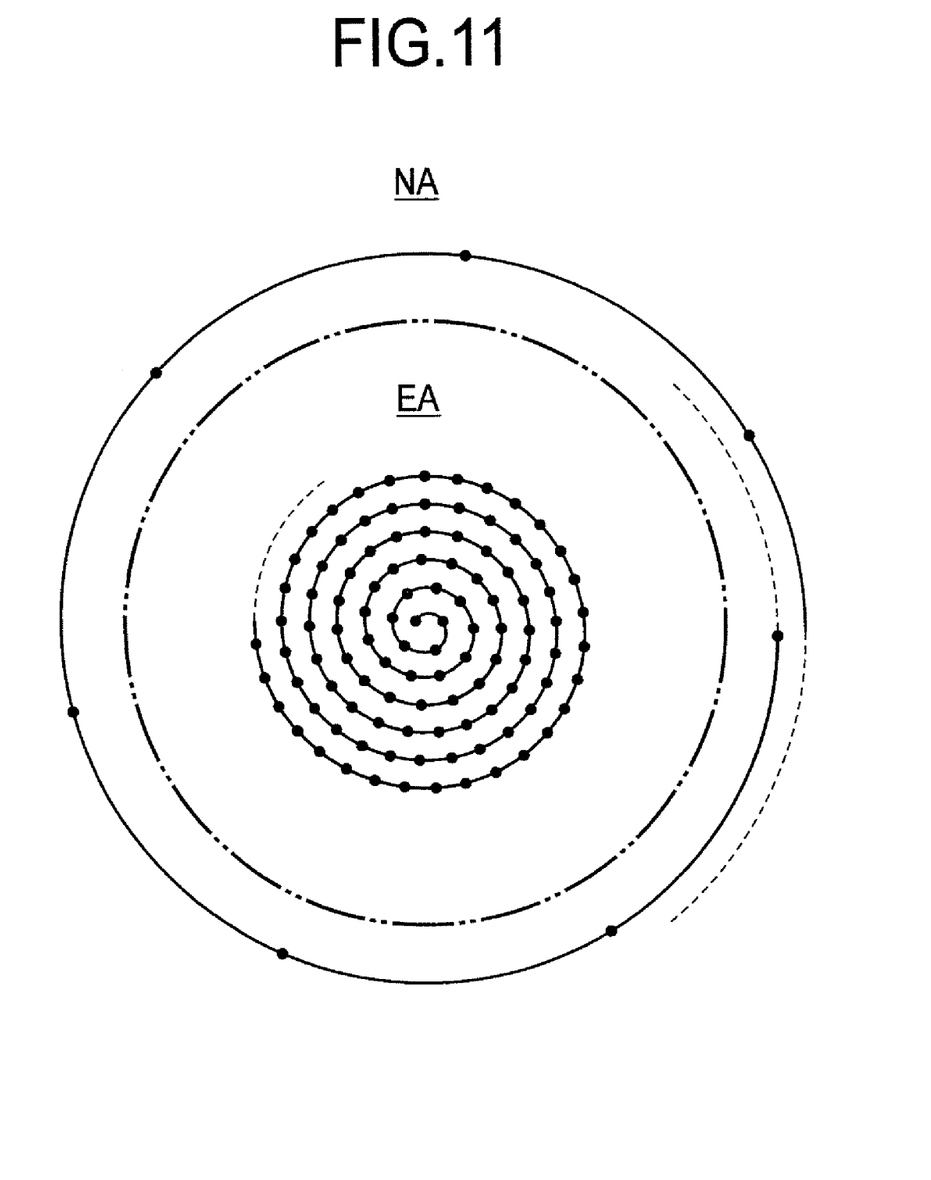
FIG. 11 shows the difference in the numbers of the pixel signals generated per a certain area size between the enlarged observation area and the normal observation area.

Accordingly, as shown in FIG. 11, the number of pixel signals generated per a certain area size for the enlarged observation area (see "EA") is 10 times as great as that for the normal observation area (see "NA").

The image processing circuit 22 stores all the received pixel signals generated when the head end of the illumination fiber 53 faces toward the points in the normal observation area at the corresponding addresses in the normal image storage area.

On the other hand, the image processing circuit 22 stores all the received pixel signals generated when the head end of the illumination fiber 53 faces toward the points in the enlarged observation area at the corresponding addresses in the enlarged image storage area. In addition, the image processing circuit 22 stores 1/10 of the received pixel signals generated when the head end of the illumination fiber 53 faces toward the points in the enlarged observation area at the corresponding addresses in the normal image storage area.

As described above, an enlarged image signal and a normal image signal, which are generated and stored in the enlarged image storage area and the normal image storage area, are transmitted to the monitor 11. The normal image corresponding to the normal image signal and the enlarged image, which is the same size as the normal image but corresponds to the enlarged image signal, are simultaneously displayed on the monitor 11 (see "NI" and "EI" in FIG. 12).

Figure 12:
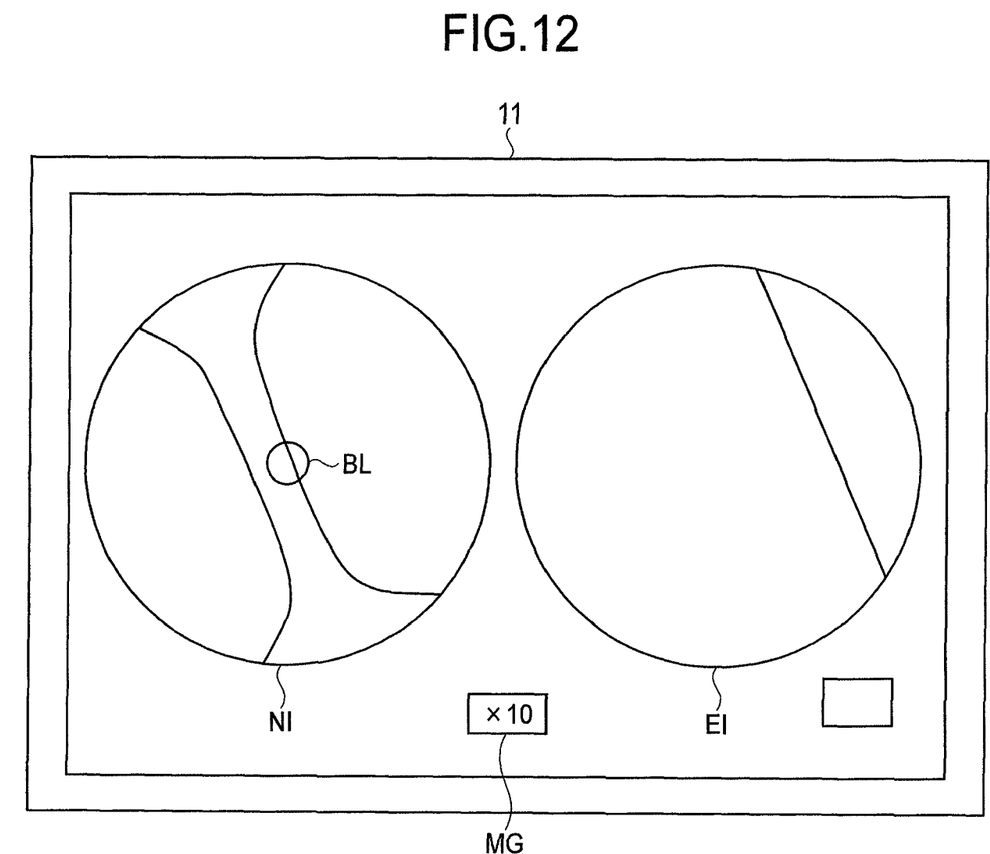
FIG. 12 illustrates the normal and enlarged images displayed on the monitor while carrying out the enlarged observation function.

In addition, a borderline indicates the area of the enlarged image that is displayed in the normal image (see "BL"). Furthermore, the magnified enlargement of the enlarged image to the normal image size is displayed also (see "MG").

The size of the enlarged observation area can be changed by inputting a command to the input block 27 for changing the size. When the size of the enlarged observation area is changed to 1/x (x being a real number greater than one) of the size of the observation area, the cycle of the A/D conversion processing is changed also. When the head end of the illumination fiber 53 faces toward the points in the newly determined enlarged observation area, the timing controller 23 adjusts the cycle of the A/D conversion processing so that the product of the cycle "t" and the distance "r" is a constant value of "k/x".

The image processing circuit 22 stores 1/x of the received pixel signals, which are generated when the head end of the illumination fiber 53 faces toward the points in the enlarged observation area, at the corresponding addresses in the normal image storage area. By storing 1/x of the pixel signals, the normal image signal is generated.

In the above embodiment, a user can simultaneously observe the enlarged image, which is a part of the normal image with enlargement, and the normal image that includes a field of vision large enough be visible on the monitor 11.

Using a prior endoscope apparatus, a section of area can be displayed with enlargement by using a signal processing technique for enlargement. However, because actual minute optical information is not gained in such a an enlarged image with great enough image resolution cannot be displayed.

On the other hand, in the above embodiment, the number of the generated pixel signals per a certain area is raised for the enlarged observation area. Accordingly, it is possible to generate an enlarged image of which image resolution is great enough.

In a prior art, there is an endoscope apparatus having two separated optical systems for the observation of normal and enlarged images, in which optical images that separately pass though the optical systems can be captured by respective image sensors or the respective optical fiber. However, in such an endoscope apparatus, because there is a parallax between the points for capturing normal and enlarged optical images, it is difficult for an observer to determine which area is displayed as the enlarged image in the full normal image. In addition, the diameter of an insertion tube of the endoscope is required to be thinner and thinner, but the diameter should be thick in this case.

On the other hand, in the above embodiment, the location of the enlarged image in the normal image is easily distinguishable owing to the borderline drawn in the normal image. In addition, because a plurality of optical systems and a plurality of optical fibers for image capturing are unnecessary, it is possible to reduce the thickness of the insertion tube compared to a prior endoscope.

The cycle of the A/D conversion processing is adjusted so that the product of the cycle of the A/D conversion processing and the distance between the head end of the illumination fiber 53 and the center of the spiral course is constant, in the above embodiment. However, the product cannot be constant. Nonetheless, the effect similar to the above embodiment can be achieved as long as the number of the generated pixel signals per a certain area size for the enlarged observation area is greater than that for the normal observation area upon carrying out the enlarged image observation function.

As described above, the product of the cycle "t", the distance "r", and the angular velocity "ω" (i.e., r×ω×t) is equivalent to the space between the points where the neighboring pixel signals are generated. In order to increase the number of generated pixel signals, the space is narrowed. Accordingly, the cycle and/or the angular velocity can be adjusted so that the space for the enlarged observation area is lower than that for the normal observation area.

For example, by carrying out the A/D conversion processing in a certain cycle by moving the head end of the illumination fiber 53 along the spiral course at the constant angular velocity, it is possible to narrow the space between the points where the neighboring pixel signals are generated for the enlarged observation area compared with that for the normal observation area. However, in such an operation, because the number of the generated pixel signals per a certain area size both for the normal and enlarged observation areas is not constant, the number of pixel signals that are deleted without being stored increases, the closer the point to generate the pixel signals is to the center in the respective observation area.

All the pixel signals are stored in the image memory upon carrying out the normal image observation function, in the above embodiment. However, all the pixel signals do not have to be stored. As described above, if the number of the generated pixel signals per a certain area size is not constant, a greater-than-necessary number of pixel signals are generated. Finally, a portion of all the generated pixel signals are stored in the image memory 25.

The enlarged observation area is defined so that the enlarged observation area includes the center of the observation area, in the above embodiment. However, an area that does not include the center can be defined as the enlarged observation area. The same effect can be achieved as long as the number of the generated pixel signals per a certain area size for the enlarged observation area is higher than that for the normal observation area.

The head end of the illumination fiber 53 is moved along the spiral course, in the above embodiment. However, it is not necessary for the course along which the head end is moved to be a spiral course. The head end may be moved along another shape of a course and an observation area can still be scanned.

Lasers are used as light sources to emit red, green, and blue light, in the above embodiment. However, other kinds of light sources may be used. But, a laser is preferable for the light source in the above embodiment because it is preferable to shine the illumination light on a minute point within an observation area of the scanning endoscope, and a laser can emit light having strong directivity.

The PMTs are used for generation of the pixel signals, in the above embodiment. However, other kinds of photoelectric converter that detect the amounts of light components, such as a photodiode, can be used.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2008-288190 (filed on Nov. 10, 2008), which is expressly incorporated herein, by reference, in its entirety.

The invention claimed is:

1. An endo scope apparatus comprising:
an imaging controller that makes an optical image to be captured so that an amount of optical information to be captured per a certain area size for an enlarged observation area is greater than that for a normal observation area, the enlarged observation area being a part of an area defined in an observation area of which an optical image should be generated, the normal observation area being the observation area excluding the enlarged observation area;
a receiver that receives the optical information as a pixel signal, the pixel signal being an electric signal;
an image generator that generates a normal image signal corresponding to a normal image on the basis of the pixel signals captured within the normal observation area and a part of the pixel signals captured within the enlarged observation area, the image generator generating an enlarged image signal corresponding to an enlarged image on the basis of the pixel signals captured within the enlarged observation area, the normal image and the enlarged image being images of the normal and enlarged observation areas, respectively,
a scanning endo scope that has first and second channels and an actuator, the first channel transmitting illumination light and making the illumination light incident on the observation area, the second channel transmitting the optical information at locations illuminated by the illumination light incident from the first channel, the actuator moving the first channel so that the observation area is scanned with the illumination light incident from the first channel; and
a photoelectric converter that captures the optical information transmitted by the second channel and generates the pixel signal according to an amount of light corresponding to the optical information,
the imaging controller controlling the actuator to move the first channel along a spiral course, and the photoelectric converter to generate the pixel signals at locations illuminated by the illumination light during scanning, and
the receiver receiving the pixel signals from the photoelectric converter,
wherein the imaging controller controls at least one of the actuator and the photoelectric converter so that the product of a first angular velocity, a first distance and a first cycle, for the enlarged observation area is greater than the product of the first angular velocity, the first distance and the first cycle, for the normal observation area, the first channel being moved along the spiral course at the first angular velocity, the first distance being a distance between a point of the first channel on the spiral course and the center of the spiral course, the photoelectric converter generating the pixel signals in the first cycle.

2. An endoscope apparatus according to claim 1, wherein, a circular area having a center that corresponds with a point on the observation area corresponding to the center of the spiral course is defined as the enlarged observation area, and
the imaging controller controls the actuator to move the first channel along the spiral course at a constant angular velocity, and the photoelectric converter to generate the pixel signals in a constant cycle.

3. An endo scope apparatus according to claim 1, further comprising an image memory that has a normal image storage area and an enlarged image storage area, a plurality of the pixel signals forming the normal image signal being stored at corresponding addresses in the normal image storage area, a plurality of the pixel signals forming the enlarged image signal being stored at corresponding addresses in the enlarged image storage area,
the image generator generating the normal image by storing the pixel signals received by the receiver in the normal image storage area, the image generator generating the enlarged image by storing the pixel signals received by the receiver in the enlarged image storage area, the pixel signals being stored at the addresses corresponding to the locations at which the optical information appears.

4. An endoscope apparatus according to claim 1, further comprising a monitor on which the normal image and the enlarged image are simultaneously displayed.

5. A scanning endoscope processor, the scanning endoscope processor controlling a scanning endo scope having first and second channels and an actuator, the scanning endo scope processor comprising:
- a first controller that controls the actuator to move the first channel along a spiral course, the first channel transmitting illumination light and making the illumination light incident on an observation area of which an optical image is generated, the actuator moving the first channel so that the observation area is scanned with the illumination light incident from the first channel;
- a photoelectric converter that captures optical information transmitted by the second channel and generates pixel signals according to an amount of light corresponding to the optical information, the second channel transmitting the optical information at locations illuminated by the illumination light incident from the first channel;
- a second controller that adjusts at least one of a first velocity and a first cycle so that a number of pixel signals generated per a certain area size for an enlarged observation area is greater than that for a normal observation area, the first channel being moved at the first velocity, the photoelectric converter generating the pixel signals in the first cycle, the enlarged observation area being a part of an area defined in an entire observation area of which the optical image is generated, the normal observation area being the observation area excluding the enlarged observation area; and
- an image generator that generates a normal image signal corresponding to a normal image on the basis of the pixel signals captured within the normal observation area and a part of the pixel signals captured within the enlarged observation area, the image generator generating an enlarged image signal corresponding to an enlarged image on the basis of the pixel signals captured within the enlarged observation area, the normal image and the enlarged image being images of the normal and enlarged observation areas, respectively, wherein the first controller controls the photoelectric converter to generate the pixel finals at the locations illuminated by the illumination light during scanning, and wherein the first controller controls at least one of the actuator and the photoelectric converter so that the product of a first angular velocity, a first distance and the first cycle, for the enlarged observation area is greater than the product of the first angular velocity, the first distance and the first cycle, for the normal observation area, the first channel being moved along the spiral course at the first angular velocity, the first distance being a distance between a point of the first channel on the spiral course and the center of the spiral course.

6. The scanning endo scope processor according to claim 5, wherein
- a circular area having a center that corresponds with a point on the observation area corresponding to the center of the spiral course is defined as the enlarged observation area, and
- the first controller controls the actuator to move the first channel along the spiral course at a constant angular velocity, and the photoelectric converter to generate the pixel signals in a constant cycle.

* * * * *